United States Patent [19]

Arahori et al.

[11] Patent Number: 5,242,894
[45] Date of Patent: Sep. 7, 1993

[54] N-SUBSTITUTED-3-(NITROGEN-CONTAINING 5-MEMBERED RING)-BENZENESULFONAMIDE DERIVATIVES, AND HERBICIDAL COMPOSITIONS

[75] Inventors: Hideo Arahori; Shiro Yamazaki; Masato Arahira; Aiko Murakami, all of Iwaki, Japan

[73] Assignee: Kureha Kagaku Kogyo K.K., Japan

[21] Appl. No.: 871,659

[22] Filed: Apr. 21, 1992

Related U.S. Application Data

[62] Division of Ser. No. 473,809, Feb. 2, 1990, Pat. No. 5,127,937.

[30] Foreign Application Priority Data

Feb. 8, 1989 [JP] Japan ................... 1-27368

[51] Int. Cl.$^5$ ............... C07D 239/69; A01N 43/54
[52] U.S. Cl. .................. 504/215; 544/321; 544/332
[58] Field of Search ............ 71/92; 544/321, 331; 504/215

[56] References Cited

U.S. PATENT DOCUMENTS 4,225,337  9/1980  Levitt .......................... 71/93
4,369,058  1/1983  Levitt .......................... 544/320

FOREIGN PATENT DOCUMENTS 116518    8/1984   European Pat. Off.
162723   11/1985   European Pat. Off.
2112783  11/1985   United Kingdom.
2112784   2/1986   United Kingdom.

OTHER PUBLICATIONS

Morrison and Boyd, "Five-Membered Rings", Organic Chemistry, 5th Ed., Chapter 35, pp. 1208–1215 (1987).
Merck Index, 11th Ed., p. 1274, #8026 (1989).

Primary Examiner—John M. Ford
Attorney, Agent, or Firm—Lowe, Price, LeBlanc & Becker

[57] ABSTRACT

Disclosed herein are N-substituted-3-(nitrogen-containing 5-membered ring)benzenesulfonamide derivatives of the formula (I):

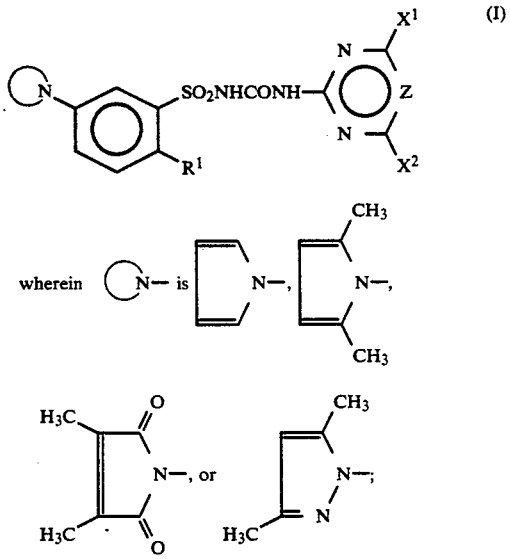

$R^1$ is H, Cl, $C_1$–$C_3$ alkyl or $C_1$–$C_4$ alkoxycarbonyl; Z is CH or N; $X^1$ is $C_1$–$C_3$ is alkyl, $C_1$–$C_3$ alkoxyl or Cl; and $X^2$ is $C_1$–$C_3$ alkyl or $C_1$–$C_3$ alkoxyl, a process for the preparation thereof, and herbicidal compositions containing the N-substituted-3-(nitrogen-containing 5-membered ring)benzenesulfonamide derivatives as active ingredients.

9 Claims, No Drawings

N-SUBSTITUTED-3-(NITROGEN-CONTAINING 5-MEMBERED RING)-BENZENESULFONAMIDE DERIVATIVES, AND HERBICIDAL COMPOSITIONS

This application is a division of U.S. application Ser. No. 07/473,809, filed Feb. 2, 1990, now U.S. Pat. No. 5,127,938.

BACKGROUND OF THE INVENTION

1) Field of the Invention

The present invention relates to N-substituted-3-(nitrogen-containing 5-membered ring)benzenesulfonamide derivatives, a preparation process thereof, and herbicidal compositions containing the derivatives as active ingredients.

2) Description of the Related Art

Numerous compounds have heretofore been proposed as herbicides. Regarding N-substituted benzenesulfonamide derivatives, a variety of compounds has also been reported as herbicides. N-substituted benzenesulfonamides containing a 5-membered ring bonded to the benzene ring and a pyrimidine ring or 1,3,5-triazine ring bonded to the nitrogen atom include, for example, the compounds of the following formula disclosed in GB 2 112 784 A and GB 2 112 783 A:

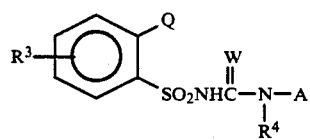

wherein Q is a 5-membered ring, $R^3$ is H, F, Cl, Br, $CH_3$, $CF_3$ or $OCH_3$, $R^4$ is H or $CH_3$, W is O or S,

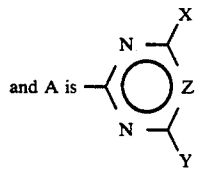

in which X is $CH_3$, $OCH_3$ or Cl, Y is $CH_3$, $C_2H_5$, $CH_2OCH_3$, $OCH_3$, $OC_2H_5$ or the like, and Z is CH or N.

There have conventionally been strong demands for herbicides capable of exhibiting reliable herbicidal activity even at such low application dosages as bringing about the advantage of reducing the amount present in the environment, herbicides capable of exhibiting selectivity between crops and weeds irrespective of variations in environmental conditions, herbicides free from crop injury to the second crop in double cropping, etc. The present invention has been completed with a view toward meeting such demands.

The present inventors have found that a series of compounds having a 5-membered ring on the 3-position of benzenesulfonamide as opposed to the inclusion of a 5-membered ring on the 2-position of benzenesulfonamide in the compounds disclosed in GB 2 112 784 A and GB 2 112 783 A referred to above has excellent herbicidal activity, leading to the completion of the present invention.

SUMMARY OF THE INVENTION

Therefore, an object of the invention is to provide novel compounds which show excellent herbicidal activity.

Another object of the invention is to provide a process for preparing novel compounds which show excellent herbicidal activity.

A further object of the invention is to provide intermediates useful in the preparation of novel compounds which show excellent herbicidal activity.

A still further object of the invention is to provide novel herbicidal compositions which show excellent herbicidal activity.

A still further object of the invention is to provide a method for controlling monocotyledonous or dicotyledonous weeds on an agricultural or nonagricultural land.

In one aspect of the invention, there is thus provided an N-substituted-3-(nitrogen-containing 5-membered ring)benzenesulfonamide derivative of the formula (I):

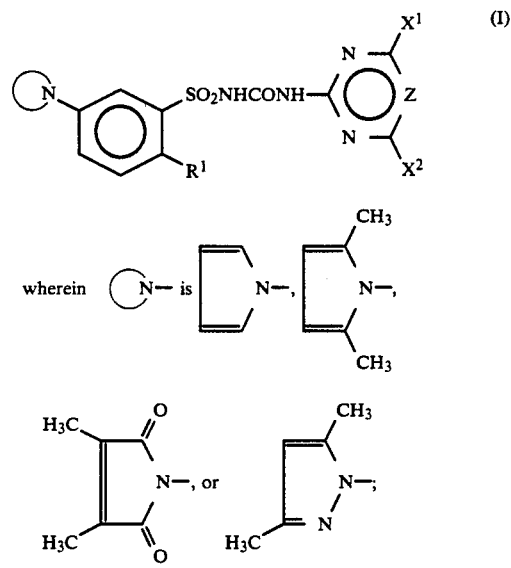

$R^1$ is H, Cl, $C_1$-$C_3$ alkyl or $C_1$-$C_4$ alkoxycarbonyl; Z is CH or N; $X^1$ is $C_1$-$C_3$ alkyl, $C_1$-$C_3$ alkoxyl or Cl; and $X^2$ is $C_1$-$C_3$ alkyl or $C_1$-$C_3$ alkoxyl.

In another aspect of the invention, there is also provided a process for the preparation of the above N-substituted-3-(nitrogen-containing 5-membered ring)benzenesulfonamide derivative, which comprises reacting a 3-(nitrogen-containing 5-membered ring) benzenesulfonamide derivative of the formula (II):

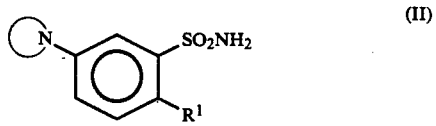

wherein

and R¹ have the same meanings as defined above, with a phenylcarbamate derivative of the following formula (III):

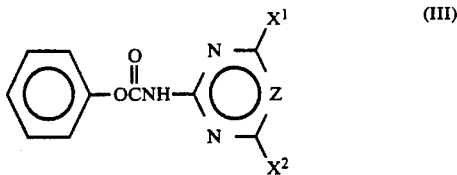

wherein Z, X¹ and X² have the same meanings as defined above.

In a further aspect of the invention, there is also provided a 3-(pyrrol-1-yl)benzenesulfonamide derivative useful as an intermediate in the preparation of the above N-substituted-3-(nitrogen-containing 5-membered ring)benzenesulfonamide, which is represented by the following formula (II-A):

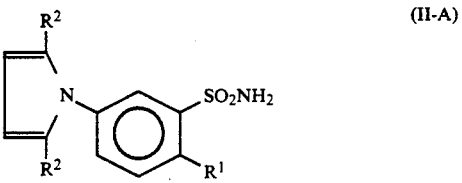

wherein R¹ has the same meaning as defined above and R² is H or $CH_3$.

In a still further aspect of the invention, there is also provided a 3-(2,3-dimethylmaleimido)benzenesulfonamide derivative useful as an intermediate in the preparation of the above N-substituted-3-(nitrogen-containing 5-membered ring)benzenesulfonamide, which is represented by the following formula (II-B):

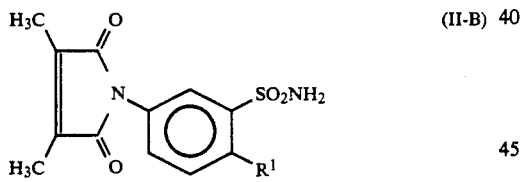

wherein R¹ has the same meaning as defined above.

In a still further aspect of the invention, there is also provided a 3-(3,5-dimethylpyrazol-1-yl)benzenesulfonamide derivative useful as an intermediate in the preparation of the above N-substituted-3-(nitrogen-containing 5-membered ring)benzenesulfonamide, which is represented by the following formula (II-C'):

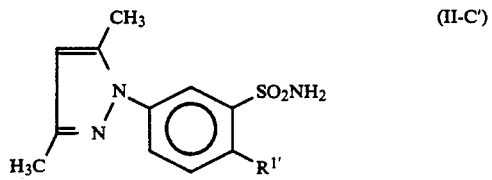

wherein $R^{1'}$ is $C_1$-$C_4$ alkoxycarbonyl.

In a still further aspect of the invention, there is also provided a herbicidal composition comprising a herbicidally effective amount of an N-substituted-3-(nitrogen-containing 5-membered ring)benzenesulfonamide derivative of the formula (I) and an agronomically-acceptable vehicle or diluent.

In a still further aspect of the invention, there is also provided a method for the control of monocotyledonous or dicotyledonous weeds on an agricultural or nonagricultural land, which comprises applying to the agricultural or non-agricultural land the N-substituted-3-(nitrogen-containing 5-membered ring)benzenesulfonamide derivative of the formula (I) or a herbicidal composition comprising said derivative.

The N-substituted-3-(nitrogen-containing 5-membered ring)benzenesulfonamide derivatives of the present invention, which are represented by the formula (I), exhibit reliable herbicidal activity at low application dosages and show selectivity between crops and weeds. The herbicidal compositions of the invention, which contain the above derivatives as effective ingredients, are suitable particularly for controlling before or after germination dicotyledonous and/or monocotyledonous weeds in important crops, for example, such as wheat, rice, corn, soybean, cotton, beet, potato, tomato or the like. They are also usable for the control of weeds not only on agricultural lands such as upland fields, paddy fields and orchards but also on non-agricultural lands such as athletic fields and factory sites.

DETAILED DESCRIPTION OF PREFERRED EMBODIMENTS

Specific examples of the N-substituted-3-(nitrogen-containing 5-membered ring)benzenesulfonamide derivative represented by the formula (I) in the invention include those shown in Table 1.

TABLE 1

| Compound No. | ⟨N— | R¹ | X¹ | X² | Z |
|---|---|---|---|---|---|
| I-1 | pyrrol-1-yl | H | OCH₃ | OCH₃ | CH |
| I-2 | 2,5-dimethylpyrrol-1-yl | H | OCH₃ | OCH₃ | CH |
| I-3 | pyrrol-1-yl | Cl | OCH₃ | OCH₃ | CH |
| I-4 | 2,5-dimethylpyrrol-1-yl | Cl | OCH₃ | CH₃ | CH |

TABLE 1-continued

[Structure: pyrrole-N-phenyl-SO2NHCONH-pyrimidine/triazine with X1, X2, Z, R1 substituents]

| Compound No. | ⟨N— ring | R¹ | X¹ | X² | Z |
|---|---|---|---|---|---|
| I-5 | pyrrol-1-yl | CH₃ | OCH₃ | OCH₃ | CH |
| I-6 | 2,5-dimethylpyrrol-1-yl | CH₃ | OCH₃ | OCH₃ | CH |
| I-7 | pyrrol-1-yl | COOCH₃ | OCH₃ | OCH₃ | CH |
| I-8 | 2,5-dimethylpyrrol-1-yl | COOCH₃ | OCH₃ | OCH₃ | CH |
| I-9 | pyrrol-1-yl | COOC₂H₅ | OCH₃ | OCH₃ | CH |
| I-10 | 2,5-dimethylpyrrol-1-yl | COOC₂H₅ | OCH₃ | OCH₃ | CH |
| I-11 | pyrrol-1-yl | COOCH₃ | Cl | OCH₃ | CH |
| I-12 | pyrrol-1-yl | COOCH₃ | CH₃ | CH₃ | CH |
| I-13 | pyrrol-1-yl | Cl | OCH₃ | CH₃ | N |
| I-14 | pyrrol-1-yl | COOCH₃ | OCH₃ | CH₃ | N |
| I-15 | 3,4-dimethylmaleimido | H | OCH₃ | OCH₃ | CH |
| I-16 | 3,4-dimethylmaleimido | Cl | OCH₃ | OCH₃ | CH |
| I-17 | 3,4-dimethylmaleimido | CH₃ | OCH₃ | OCH₃ | CH |
| I-18 | 3,4-dimethylmaleimido | COOCH₃ | OCH₃ | OCH₃ | CH |
| I-19 | 3,5-dimethylpyrazol-1-yl | Cl | OCH₃ | OCH₃ | CH |
| I-20 | 3,5-dimethylpyrazol-1-yl | COOCH₃ | OCH₃ | OCH₃ | CH |

The N-substituted-3-(nitrogen-containing 5-membered)benzenesulfonamide derivatives represented by the formula (I) can each be synthesized by reacting a 3-(nitrogen-containing 5-membered ring)benzenesulfonamide derivative of the formula (II) and a phenylcarbamate derivative of the following formula (III) in the presence of a base and in an organic solvent in accordance with the following reaction formula:

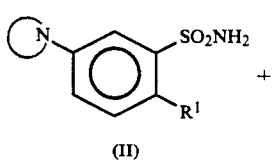

(II)

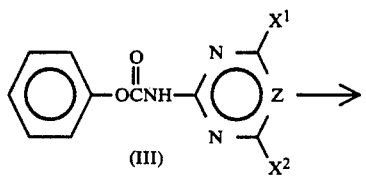

(III)

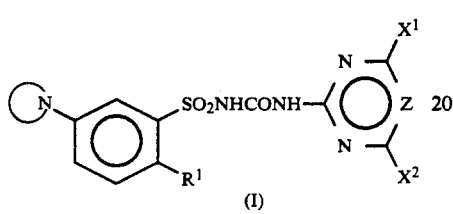

(I)

wherein

$R^1$, Z, $X^1$ and $X^2$ have the same meanings as defined above.

In the above reaction, N,N-dimethylacetamide, N-methylpyrrolidone, acetonitrile or the like can be used as an organic solvent. On the other hand, diazabicyclooctane, diazabicyclononene, diazabicycloundecene or the like can be used as a base.

The reaction is conducted at a temperature in a range of from −20° C. to 100° C., preferably from 0° C. to 50° C. for a reaction period in a range of from 0.5 hour to 24 hours.

After completion of the reaction, the reaction mixture is added to an aqueous solution of dilute hydrochloric acid and the precipitate thus formed is collected by filtration. The precipitate is dried in air and then purified by a purification technique such as reprecipitation or column chromatography or by a washing technique, whereby the intended N-substituted-3-(nitrogen-containing 5-membered ring)benzenesulfonamide derivative represented by the formula (I) can be obtained with high purity.

The 3-(nitrogen-containing 5-membered ring)benzenesulfonamide derivative represented by the formula (II), which is a preparation intermediate and is employed as the starting material in the above reaction, can be synthesized in accordance with any of the following reaction formulae (A), (B) and (C), using as a starting material a known 3-aminobenzenesulfonamide derivative represented by the following formula (IV):

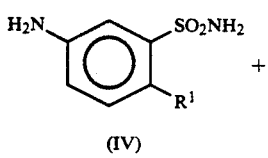

(IV)

(A)

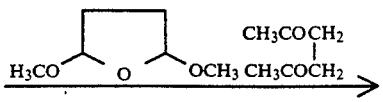

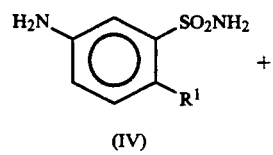

(II-A)

(B)

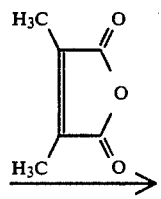

(IV)

+

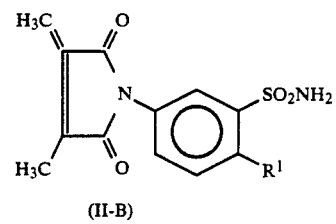

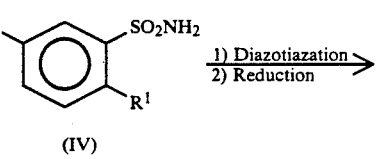

(II-B)

(C)

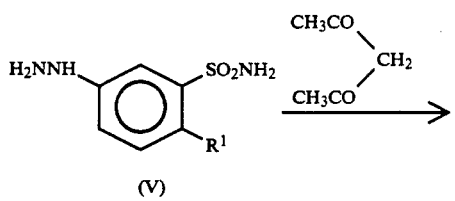

(IV)

1) Diazotiazation
2) Reduction

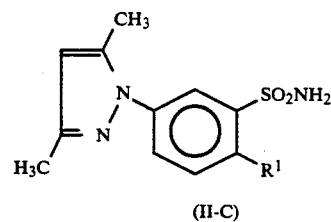

(V)

(II-C)

wherein $R^1$ and $R^2$ have the same meanings as defined above.

Synthesis of the compound represented by the formula (II-A) in accordance with the reaction formula (A) can be practiced in the following manner. A compound represented by the formula (IV) and a 2,5-dialkoxytetrahydrofuran or acetonylacetone are stirred at 50°–120° C. for 0.5–10 hours in acetic acid or propionic acid or in dioxane which contains 35% hydrochloric acid or 95% sulfuric acid in a catalytic amount. After completion of the reaction, the solvent is distilled off thoroughly, and the residue is washed with water and is then collected by filtration. The residue is then purified by column chromatography, whereby the compound represented by the formula (II-A) can be obtained with good purity.

Synthesis of the compound represented by the formula (II-B) in accordance with the reaction formula (B) can be practiced in the following manner. A compound represented by the formula (IV) and 2,3-dimethylmaleic anhydride are stirred at 50°–120° C. for 5–60 hours in pyridine, acetic acid or propionic acid. The solvent is then distilled off, followed by the addition of ice water to the residue. Subsequent to acidification when pyridine was used, the resultant mixture is thoroughly stirred, and the resulting solid matter is collected by filtration and then dried in air, so that the compound represented by the formula (II-B) can be obtained with good purity.

Synthesis of the compound represented by the formula (II-C) in accordance with the reaction formula (C) can be practiced in the following manner. The compound represented by the formula (V), which has been obtained by diazotizing the amino group of the compound represented by the formula (IV) and reducing the thus-diazotized derivative, and acetylacetone are stirred at 40°–120° C. for 3–20 hours in acetic acid or propionic acid or in an alcohol, such as methanol or ethanol, containing 35% hydrochloric acid of 95% sulfuric acid. After completion of the reaction, ice water is added to the reaction mixture and the pH of the mixture thus obtained is adjusted to pH 6. The precipitate thus formed is collected by filtration, dried in air and if necessary, purified by column chromatography, whereby the compound represented by the general formula (II-C) can be obtained with good purity.

The compounds represented by the formula (IV), which were used in the above reaction formulae (A)–(C), can be obtained from the corresponding nitrobenzene derivatives, for example, by using the process described in Bull. Chem. Soc. Jpn., 55, 3824 (1982); or from the corresponding 3-nitroaniline derivatives, for example, by the process described in Chem. Ber., 90, 841 (1957) or J. Macromol. Sci. Chem., 1969, 941, namely, by synthesizing 3-nitrobenzenesulfonamide derivatives and then reducing the nitro groups into amino groups with $SnCl_2$ in methanol or ethanol containing 35% hydrochloric acid.

Further, the compound represented by the formula (III) can be obtained from phenyl chloroformate and the corresponding 2-amino-4,6-di-substituted pyrimidine (or 1,3,5-triazine), for example, by the process described in European Patent Specification No. 238,070.

Specific examples of the compounds represented by the formulae (II-A), (II-B) and (II-C) and useful as preparation intermediates are summarized in Table 2 to Table 4, respectively.

In addition, specific examples of the compound represented by the formula (V) are shown in Table 5.

TABLE 2

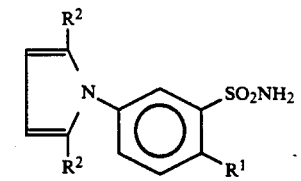

| Compound No. | $R^1$ | $R^2$ |
|---|---|---|
| II-A-1 | H | H |
| II-A-2 | H | $CH_3$ |
| II-A-3 | Cl | H |
| II-A-4 | Cl | $CH_3$ |
| II-A-5 | $CH_3$ | H |
| II-A-6 | $CH_3$ | $CH_3$ |
| II-A-7 | $COOCH_3$ | H |
| II-A-8 | $COOCH_3$ | $CH_3$ |
| II-A-9 | $COOC_2H_5$ | H |
| II-A-10 | $COOC_2H_5$ | $CH_3$ |

TABLE 3

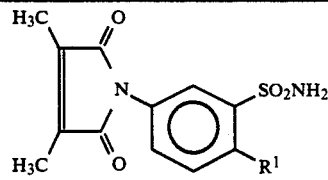

| Compound No. | $R^1$ |
|---|---|
| II-B-1 | H |
| II-B-2 | Cl |
| II-B-3 | $CH_3$ |
| II-B-4 | $COOCH_3$ |

TABLE 4

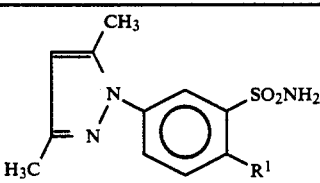

| Compound No. | $R^1$ |
|---|---|
| II-C-1 | Cl |
| II-C-2 | $COOCH_3$ |

TABLE 5

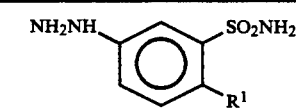

| Compound No. | $R^1$ |
|---|---|
| V-1 | H |
| V-2 | Cl |
| V-3 | $CH_3$ |
| V-4 | $COOCH_3$ |
| V-5 | $COOC_2H_5$ |

The N-substituted-3-(nitrogen-containing 5-membered ring)benzenesulfonamide derivatives exhibit reliable herbicidal activity at low application dosages and show selectivity between crops and weeds. The herbicidal compositions of the invention, which contain the above compounds as effective ingredients, are therefore suitable for controlling either before or after emergence monocotyledonous weeds and/or dicotyledonous weeds in important crops such as wheat, rice, corn, soybean, cotton, beet, potato and tomato.

Exemplary dicotyledonous weeds which can be controlled by the above N-substituted-3-(nitrogen-containing 5-membered ring)benzenesulfonamide derivatives of the invention include Amaranthus, Bidens, Stellaria, Solanum, Abutilon, Convolvulus, Matricaria, Galium, Lindernia, etc.

Illustrative monocotyledonous weeds include Echinochloa, Setaria, Digitaria, Avena, Cyperus, Alisma, Monochoria, etc.

The herbicidal compositions of the invention may take any preparation forms such as wettable powder, emulsion, powder, granule and the like. Known agronomically-acceptable vehicles (diluents) and aids can be used.

The applicable places of the N-substituted-3-(nitrogen-containing 5-membered ring)benzenesulfonamide derivatives and herbicidal compositions according to the invention range from agricultural lands such as upland fields, paddy fields and orchard to non-agricultural lands such as athletic fields and factory sites.

EXAMPLES

The present invention will hereinafter be described by the following examples.

SYNTHESIS EXAMPLE 1

Synthesis of methyl 2-[(4,6-dimethoxypyrimidin-2-yl)aminocarbonylaminosulfonyl]-4-(1H-pyrrol-1-yl)benzoate (Compound No. I-7)

At room temperature, 141.5 mg (0.5 mmol) of methyl 2-(aminosulfonyl)-4-(1H-pyrrol-1-yl)benzoate and 137.5 mg (0.5 mmol) of phenyl (4,6-dimethoxypyrimidin-2-yl)carbamate were dissolved in 1.5 ml of N,N-dimethylacetamide. Then, 82.1 mg of 1,8-diazabicyclo[5.4.0]undec-7-ene were added, followed by stirring for 5 minutes. The resultant mixture was allowed to stand for 15 hours. Thereafter, 0.2 ml of 35% hydrochloric acid was added to 20 ml of ice water, followed by the addition of the reaction mixture in 0.2 ml portions under stirring. After the reaction mixture was stirred for 20 minutes, the resulting precipitate was collected by filtration and dried in air. Using dichloromethane and petroleum ether, the crude product was purified by reprecipitation into a white solid. Yield: 196 mg (85%). Its physicochemical properties are shown in Table 6.

SYNTHESIS EXAMPLE 2

Synthesis of methyl 2-[(4-methoxy-6-methyl-1,3,5-triazin-2-yl)aminocarbonylaminosulfonyl-4-(1H-pyrrol-1-yl)benzoate (Compound No. I-14)

At room temperature, 100 mg (0.36 mmol) of methyl 2-(aminosulfonyl)-4-(1H-pyrrol-1-yl)benzoate and 85.7 mg (0.33 mmol) of phenyl (4-methoxy-6-methyl-1,3,5-triazin-2-yl)carbamate were dissolved in 1.5 ml of N,N-dimethylacetamide. Then, 65.7 mg (0.43 mmol) of 1,8-diazabicyclo[5.4.0]undec-7-ene were added, followed by stirring for 5 minutes. The resultant mixture was allowed to stand for 4 hours. Thereafter, 0.2 ml of 35% hydrochloric acid was added to 20 ml of ice water, followed by the addition of the reaction mixture in 0.2 ml portions under stirring. After the reaction mixture was stirred for 20 minutes, the resulting precipitate was collected by filtration and dried in air. Using dichloromethane and hexane, the crude product was purified by reprecipitation into a pale yellow solid. Yield: 79.5 mg (54%). Its physicochemical properties are shown in Table 6.

The other N-substituted-3-(nitrogen-containing 5-membered ring)benzenesulfonamide derivatives shown in Table 1 were also synthesized in a similar manner to Synthesis Example 1. Namely, after obtaining crude products by a similar procedure to Synthesis Example 1, they were separately purified by chromatography on a silica gel column, reprecipitation or washing. Physicochemical properties of each of the N-substituted-3-(nitrogen-containing 5-membered ring)benzenesulfonamide derivatives are shown in Table 6. Incidentally, in Table 6 and Table 10 which will be given subsequently, the abbreviations in the columns for NMR data have the following meanings:

δ: (ppm), s: singlet, d: doublet, t: triplet, q: quartet, m: multiplet, dd: double doublet, br: broad.

Further, with respect to the individual N-substituted-3-(nitrogen-containing 5-membered ring)benzenesulfonamide derivatives, the solvents employed and the yields attained were as follows:

| Compound No. | Solvent employed | Yield (%) |
|---|---|---|
| Compounds purified by column chromatography: | | |
| I-2 | $CH_2Cl_2$ | 48 |
| I-4 | $CH_2Cl_2$ | 68 |
| I-6 | $CH_2Cl_2$ | 73 |
| I-18 | $CH_2Cl_2$ | 39 |
| Compounds purified by reprecipitation: | | |
| I-9 | $CH_2Cl_2$ + petroleum ether | 74 |
| I-12 | $CH_2Cl_2$ + hexane | 81 |
| I-13 | $CH_2Cl_2$ + hexane | 56 |
| I-14 | $CH_2Cl_2$ + hexane | 54 |
| I-15 | $CH_2Cl_2$ + petroleum ether | 61 |
| I-20 | $CH_2Cl_2$ + petroleum ether | 68 |
| Compounds purified by washing: | | |
| I-1 | $CH_2Cl_2$ + petroleum ether | 61 |
| I-3 | $CH_2Cl_2$ + petroleum ether | 68 |
| I-5 | petroleum ether | 57 |
| I-7 | petroleum ether | 85 |
| I-8 | $CH_2Cl_2$ + petroleum ether | 53 |
| I-10 | $CH_2Cl_2$ + petroleum ether | 76 |
| I-11 | $CH_2Cl_2$ + hexane | 78 |
| I-16 | $CH_2Cl_2$ + petroleum ether | 64 |
| I-17 | $CH_2Cl_2$ + petroleum ether | 72 |
| I-19 | $CH_2Cl_2$ + petroleum ether | 73 |

TABLE 6

| Compound No. | MS (m/e) (A)* | MS (m/e) (B)** | Melting Point or Decomposition Point (°C.) | IR (KBr, $cm^{-1}$) | NMR (δ) | |
|---|---|---|---|---|---|---|
| I-1 | 248 | 155 | 211–213 | 3250–2600, 1720, 1600, 1580, 1490 1450, 1360, 1330, 1190, 1170, 1060, 780, 720, 580 | $d_6$-DMSO | 3.916(6H, s) 5.998(1H, s) 6.325(2H, s) 7.460(2H, s) 7.721(1H, t, 7.93Hz) 7.879(1H, d, 7.93Hz) 7.921(1H, d, 7.93Hz) 8.085(1H, s) 10.954 (1H, s) 12.657(1H, s) |
| I-2 | 276 | 155 | 192–196 | 3300–2600, 1700, 1610, 1570, 1490, 1450, 1360, 1220, 1190, 1170, 570, | $CDCl_3$ | 2.048(6H, s) 3.949(6H, s) 5.787(1H, s) 5.919(2H, s) 7.260(1H, s) 7.498(1H, d, 7.93Hz) 7.657 |

TABLE 6-continued

| Compound No. | MS (m/e) (A)* | (B)** | Melting Point or Decomposition Point (°C.) | IR (KBr, cm$^{-1}$) | NMR (δ) |
|---|---|---|---|---|---|
| | | | | 520 | (1H, t, 7.93Hz) 7.994(1H, s) 8.147(1H, d, 7.93Hz) 12.730(1H, s) |
| I-3 | 282 | 155 | 194–197 | 3250–2500, 1710, 1610, 1560, 1490, 1450, 1350, 1330, 1200, 1170, 820, 720, 580, 510, 500 | CDCl$_3$ 3.971(6H, s) 5.817(1H, s) 6.388(2H, t, 1.83Hz) 7.130 (2H, t, 1.83Hz) 7.240(1H, s) 7.545(2H, s) 8.336(1H, s) 13.035(1H, s) |
| I-4 | 310 | 155 | 197–201 | 3250–2500, 1700, 1600, 1570, 1440, 1370, 1350, 1210, 1160, 1035, 1025, 820, 810, 760, 580 | CDCl$_3$ 2.079(6H, s) 3.971(6H, s) 5.817(1H, s) 5.924(2H, s) 7.228(1H, s) 7.418(1H, dd, 8.54Hz, 2.44Hz) 7.604(1H, d, 8.54Hz) 8.199(1H, d, 2.44Hz) 13.011(1H, s) |
| I-5 | 262 | 155 | 215–217 Decomposed | 3400, 3270–2600, 1710, 1610, 1570, 1500, 1450, 1360, 1330, 1190, 1160, 820, 730, 580, 510 | CDCl$_3$ 2.677(3H, s) 3.961(6H, s) 5.809(1H, s) 6.364(2H, t, 1.8Hz) 7.130(2H, t, 1.8Hz) 7.181(1H, s) 7.355(1H, d, 8.54Hz) 7.524(1H, dd, 8.54Hz, 2.45Hz) 8.256(1H, d, 2.45Hz) 12.747(1H, s) |
| I-6 | 290 | 155 | 177–181 | 3310, 3100–2600, 1720, 1610, 1570, 1490, 1440, 1370, 1350, 1190, 1160, 750, 580, 510 | CDCl$_3$ 2.060(6H, s) 2.736(3H, s) 3.957(6H, s) 5.805(1H, s) 5.905(2H, s) 7.235(1H, s) 7.32–7.38(2H, m) 8.092(1H, d, 1.87Hz) 12.738(1H, s) |
| I-7 | 306 | 155 | 158–162 | 3400–2800, 3400, 1720, 1600, 1570, 1430, 1370, 1350, 1330, 1280, 1180, 1160, 740, 720, 570 | CDCl$_3$ 3.900(3H, s) 4.013(6H, s) 5.800(1H, s) 6.410(2H, t, 1.8Hz) 7.196(1H, s) 7.215(2H, t, 1.8Hz) 7.621(1H, dd, 8.5Hz, 1.5Hz) 7.828(1H, d, 8.5Hz) 8.436(1H, d, 1.5Hz) 12.652(1H, s) |
| I-8 | 334 | 155 | 213–215 Decomposed | 3400–2700, 3400, 2950, 1730, 1700 1610, 1570, 1490, 1440, 1350, 1290, 1200, 1170, 1120, 1060, 780, 760, 580 | CDCl$_3$ 2.099)6H, s) 3.939(3H, s) 4.001(6H, s) 5.797(1H, s) 5.936(2H, s) 7.235(1H, s) 7.516(1H, dd, 7.94Hz, 1.83Hz) 7.808(1H, d, 7.94Hz) 8.286(1H, d, 1.83Hz) 12.657(1H, s) |
| I-9 | 320 | 155 | 147–151 | 3300–2700, 1720, 1600, 1570, 1500, 1440, 1360, 1280, 1200, 1170, 590 | CDCl$_3$ 1.423(3H, t, 7.32Hz) 4.047(6H, s) 4.398(2H, q, 7.32 Hz) 5.834(1H, s) 6.449(2H, t, 2.44Hz) 7.260(2H, t, 2.44Hz) 7.306(1H, s) 7.654(1H, dd, 8.54Hz, 1.83Hz) 7.855(1H, d, 8.54Hz) 8.468(1H, d, 1.83Hz) 12.681(1H, s) |
| I-10 | 348 | 155 | 215–219 | 3310, 3150–2700, 1720, 1600, 1580, 1490, 1440, 1410, 1360, 1280, 1190, 1170, 1130, 1010, 760, 580 | CDCl$_3$ 1.398(3H, t, 7.33Hz) 2.096(6H, s) 3.998(6H, s) 4.391 (2H, q, 7.33Hz) 5.792(1H, s) 5.934(2H, s) 7.242(1H, s) 7.511(1H, dd, 7.94Hz, 1.83Hz) 7.800(1H, d, 7.94Hz) 8.278(1H, d, 1.83Hz) 12.630(1H,s) |
| I-11 | 306 | 159 | 198–201 | 3300–2800, 3180, 3130, 1750, 1715, 1610, 1590, 1580, 1510, 1490, 1465, 1370, 1350, 1285, 1130, 1005, 740, 590 | CDCl$_3$ 3.933(3H, s) 4.130(3H, s) 6.410(2H, t, 2.44Hz) 6.506 (1H, s) 7.219(2H, t, 2.44Hz) 7.406(1H, s) 7.631(1H, dd, 8.54Hz, 2.44Hz) 7.852(1H, d, 8.55Hz) 8.417(1H, d, 2.44Hz) 12.145(1H, s) |
| I-12 | 306 | 123 | 174–178 Decomposed | 3300–2750, 1750, 1710, 1620, 1490, 1470, 1450, 1360, 1280, 1180, 730, 600 | CDCl$_3$ 2.504(6H, s) 3.927(3H, s) 6.398(2H, t, 2.44Hz) 6.769 (1H, s) 7.213(2H, t, 2.44Hz) 7.560(1H, s) 7.601(1H, dd, 8.55Hz, 2.44Hz) 7.811(1H, d, 8.55Hz) 8.416(1H, d, 2.44Hz) 13.289(1H, s) |
| I-13 | 282 | 140 | 174–177 | 3340, 3200–2700, 1730, 1590, 1560, 1500, 1460, 1440, 1170, 1150, 940, 820, 750, 590, 540 | CDCl$_3$ 2.587(3H, s) 4.057(3H, s) 6.390(2H, t, 2.45Hz) 7.128 (2H, t, 2.45Hz) 7.400(1H, s) 7.552(2H, s) 8.312(1H, s) 12.9(1H, s) |
| I-14 | 306 | 140 | 166–171 Decomposed | 3300–2800, 1740, 1730, 1610, 1590, 1550, 1510, 1450, 1360, 1340, 1270, 1170, 1120, 730, 580 | d$_6$-DMSO 2.500(3H, s) 3.857(3H, s) 3.998(3H, s) 6.381(2H, t, 3.05Hz) 7.506(2H, t, 3.05Hz) 7.895(1H, d, 8.54 Hz) 8.076(1H, dd, 8.54Hz, 1.84Hz) 8.196(1H, d, 1.84Hz) 11.163(1H, s) 12.63(1H, s) |
| I-15 | 306 | 155 | 182–186 | 3240–2600, 1710, 1610, 1570, 1490, 1450, 1390, 1350, 1200, 1160, 720, 630, 580 | CDCl$_3$ 2.065(6H, s) 3.949(6H, s) 5.770(1H, s) 7.220(1H, s) 7.621(1H, t, 7.93Hz) 7.715(1H, dd, 7.93Hz, 1.83Hz) 8.102(1H, dd, 7.93Hz, 1.83Hz) 8.19(1H, d, 1.83Hz) 12.672(1H, s) |
| I-16 | 340 | 155 | 126–128 Decomposed | 3300–2600, 1770, 1710, 1600, 1570, 1490, 1450, 1360, 1220, 1200, 1170, 590, 505 | CDCl$_3$ 2.072(6H, s) 3.961(6H, s) 5.800(1H, s) 7.233(1H, s) 7.562(1H, d, 8.54Hz) 7.668(1H, dd, 8.54Hz, 1.83Hz) 8.444(1H, d, 1.83Hz) 12.969br(1H, s) |
| I-17 | 320 | 155 | 174–177 Decomposed | 3300–2700, 1770, 1710, 1700, 1610, 1580, 1490, 1450, 1350, 1220, 1200, 1170, 580 | CDCl$_3$ 2.062(6H, s) 2.697(3H, s) 3.954(6H, s) 5.792(1H, s) 7.162(1H, s) 7.379(1H, d, 8.54Hz) 7.567(1H, dd, 8.54Hz, 1.5Hz) 8.286(1H, d, 1.5Hz) 12.694(1H, s) |
| I-18 | 364 | 155 | 134–138 | 3340–2800, 3100, 2950, 1720, 1600 1580, 1490, 1450, 1370, 1350, 1290, 1200, 1170, 1130, 1060, 730, 630, 590 | CDCl$_3$ 2.082(6H, s) 3.900(3H, s) 3.998(6H, s) 5.785(1H, s) 7.164(1H, s) 8.565(2H, d, 1.2Hz) 8.565(1H, d, 1.2Hz) 12.589(1H, s) |
| I-19 | 311 | 155 | 167–171 | 3230–2600, 1700, 1610, 1570, 1500, 1480, 1450, 1380, 1360, 1200, 1170, 1050, 830, 580, 520, 505 | CDCl$_3$ 2.284(3H, s) 2.424(3H, s) 3.969(6H, s) 5.812(1H, s) 6.032(1H, s) 7.242(1H, s) 7.579(1H, d, 8.54Hz) 7.792 (1H, dd, 8.54Hz, 2.44Hz) 8.356(1H, d, 2.44Hz) 13.021(1H, s) |
| I-20 | 335 | 155 | 167–171 Decomposed | 3400–2700, 2930, 1730, 1710, 1610, 1570, 1500, 1450, 1380, 1350, 1280, 1200, 1170, 1120, 1050, 990, 780, 640, | CDCl$_3$ 2.299(3H, s) 2.497(3H, s) 3.913(3H, s) 4.008(6H, s) 5.795(1H, s) 6.061(1H, s) 7.196(1H, s) 7.826(1H, d, 8.55Hz) 7.948(1H, dd, 8.55Hz, 1.83Hz) 8.452 |

TABLE 6-continued

| Compound No. | MS (m/e) (A)* | (B)** | Melting Point or Decomposition Point (°C.) | IR (KBr, cm⁻¹) | NMR (δ) |
|---|---|---|---|---|---|
| | | | | 580 | (1H, d, 1.83Hz) 12.640(1H, s) |

*) (A)

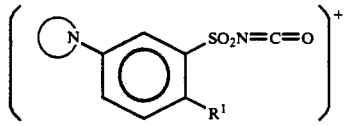

**) (B)

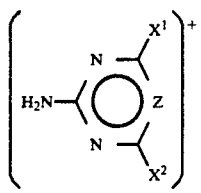

SYNTHESIS EXAMPLE 3

Synthesis of preparation intermediate, methyl 2-(aminosulfonyl1)-4-(1H-pyrrol-1-yl)benzoate (Compound No. II-A-7)

In 3 ml of acetic acid, 300 mg (1.3 mmol) of methyl 4-amino-2-(aminosulfonyl)benzoate and 0.23 ml of 2,5-dimethoxytetrahydrofuran were dissolved, followed by stirring at 110 C. for 1.5 hours. Acetic acid was then distilled off, followed by the addition of 30 ml of ice water. After the mixture thus obtained was stirred for 20 minutes, the resulting precipitate was collected by filtration and dried in air. The brown solid thus obtained was purified by column chromatography, using silica gel ("Wako Gel C-300", trade name; product of Wako Pure Chemical Industries, Ltd.) and dichloromethane, thereby obtaining the title compound as a white solid.

Yield: 175.7 mg (48%). Its physicochemical properties are shown in Table 7.

The other compounds shown in Table 7 were also synthesized in a similar manner to Synthesis Example 3. The yield and physicochemical properties of each of the compounds are also shown in Table 7.

TABLE 7

| Compound No. | Yield (%) | MS (m/e) M⁺ | Melting Point or Decomposition point (°C.) | IR (KBr, cm⁻¹) |
|---|---|---|---|---|
| II-A-1 | 42 | 222 | 158–160 | 3330, 3240, 3090, 1600, 1490, 1320, 1310, 1150, 1100, 1070, 940, 890, 800, 730, 680, 610 |
| II-A-2 | 74 | 250 | 104–107 | 3350, 3250, 3050, 2910, 1600, 1480, 1430, 1390, 1310, 1300, 1150, 920, 800, 750, 690, 590, 530 |
| II-A-3 | 69 | 256 | 154–160 | 3340, 3250, 3130, 1600, 1490, 1460, 1350, 1170, 1070, 1030, 940, 890, 840, 800, 740, 720, 700, 590, 510 |
| II-A-4 | 62 | 284 | 185–188 Decomposed | 3330, 3230, 3090, 2910, 1550, 1470, 1400, 1340, 1170, 1050, 1035, 910, 850, 770, 590, 510 |
| II-A-5 | 48 | 236 | 118–121 | 3370, 3270, 1610, 1500, 1330, 1290, 1160, 1140, 1070, 940, 720, 620, 600, 590 |
| II-A-6 | 76 | 264 | 174–177 | 3350, 3250, 3070, 2920, 1550, 1490, 1450, 1400, 1330, 1170, 1070, 920, 910, 850, 770, 720, 600, 530 |
| II-A-7 | 48 | 280 | 162–165 | 3320, 3230, 2950, 1710, 1600, 1500, 1440, 1340, 1320, 1300, 1280, 1170, 1150, 1050, 940, 870, 770, 730, 690 |
| II-A-8 | 63 | 308 | 168–170 | 3380, 3270, 2920, 1710, 1600, 1440, 1410, 1350, 1320, 1300, 1170, 1130, 780, 600 |
| II-A-9 | 62 | 294 | 156–160 | 3300, 3230, 3130, 2980, 1700, 1600, 1500, 1350, 1270, 1170, 1120, 1070, 1050, 800, 780, 740 |
| II-A-10 | 60 | 322 | 195–197 | 3370, 3260, 2980, 2920, 1700, 1600, 1400, 1350, 1320, 1300, 1160, 1150, 780, 600 |

SYNTHESIS EXAMPLE 4

Synthesis of preparation intermediate, 2-chloro-5-(2,5-dihydro-3,4-dimethyl-2,5-dioxo-1H-pyrrol-1-yl)benzenesulfonamide (Compound No. II-B-2)

In 3 ml of pyridine, 1 mmol of 5-amino-2-chlorobenzenesulfonamide and 1.05 mmol of 2,3-dimethylmaleic anhydride were stirred at 90–100° C. for 9 hours. Pyridine was then distilled off from the reaction mixture, followed by the addition of 20 ml of ice water and 0.1 ml of 35% hydrochloric acid to the solid residue. After the mixture thus formed was stirred for 20 minutes, the resulting precipitate was collected by filtration and then dried in air. Yield: 93%. Its physicochemical properties are shown in Table 8.

The other compounds (Compound No. II-B-1 to Compound No. II-B-3) shown in Table 8 were also synthesized in a manner similar to Synthesis Example 4. The yield and physicochemical properties of each of the compounds are also shown in Table 8.

tion mixture was then transferred into a 3-l beaker, to which 38 g of sodium bicarbonate were then added under stirring to adjust the pH to 6. The mixture thus prepared was then extracted twice with 300 ml of methyl acetate. The extract was dried over sodium sulfate, and methyl acetate was distilled off to obtain a pale yellow solid. Yield: 2.76 g (86%). Melting point: 168–170° C. Its physicochemical properties are shown in Table 10.

(2) Synthesis of methyl 2-(aminosulfonyl)-4-(3,5-dimethyl-1H-pyrazol-1-yl)benzoate (Compound No. II-C-2)

TABLE 8

| Compound No. | Yield (%) | MS (m/e) M+ | Melting Point or Decomposition point (°C.) | IR (KBr, cm$^{-1}$) |
| --- | --- | --- | --- | --- |
| II-B-1 | 94 | 280 | 209–211 | 3340, 3250, 1760, 1700, 1480, 1440, 1400, 1340, 1160, 1100, 790, 730, 670, 590, 520 |
| II-B-2 | 93 | 314 | 199–202 | 3350, 3250, 1760, 1700, 1470, 1400, 1390, 1340, 1170, 1080, 1040, 910, 830, 730, 710, 600, 530, 510 |
| II-B-3 | 91 | 294 | 190–192 | 3350, 3250, 1760, 1710, 1690, 1530, 1490, 1390, 1330, 1170, 1150, 1080, 900, 830, 730, 720, 610, 590 |
| II-B-4 | 43 | 338 | 159–162 | 3400–2900, 1710, 1680, 1600, 1490, 1440, 1410, 1390, 1350, 1310, 1290, 1170, 1150, 1130, 1090, 1060, 860, 780, 730, 670, 600, 530 |

SYNTHESIS EXAMPLE 5

Synthesis of preparation intermediate, methyl 2-(aminosulfonyl)-4-(2,5-dihydro-3,4-dimethyl-2,5-dioxo-1H-pyrrol-1-yl)benzoate (Compound No. II-B-4)

In 3 ml of acetic acid, 1 mmol of methyl 4-amino-2-(aminosulfonyl)benzoate and 1.05 mmol of 2,3-dimethylmaleic anhydride were stirred at 80° C. for 40 hours. Acetic acid was then distilled off from the reaction mixture, followed by the addition of 20 ml of ice water to the oily residue. After the mixture thus formed was stirred for 2 hours, the resulting precipitate was collected by filtration and then dried in air. Yield: 43%. Its physicochemical properties are shown in Table 8.

SYNTHESIS EXAMPLE 6

Synthesis of preparation intermediate, methyl 2-(aminosulfonyl)-4-(3,5-dimethyl-1H-pyrazol-1-yl)benzoate (Compound No. II-C-2)

(1) Synthesis of methyl 2-(aminosulfonyl)-4-hydrazinobenzoate (Compound No. V-4)

To a mixture of 6 ml of 35% hydrochloric acid and 6 ml of water, 3 g of methyl 4-amino-2-(aminosulfonyl)benzoate were added, followed by stirring at room temperature for 5 minutes. The reaction mixture was then cooled with ice water, followed by the addition of 3 ml of an aqueous solution of 0.95 g of sodium nitrite under stirring over 2 minutes to conduct diazotization.

In 6.52 ml of 35% hydrochloric acid, 6.78 g of stannous chloride were dissolved. The resulting solution was cooled with ice water and stirred, followed by the addition of the diazotized compound prepared above.

After the resultant mixture was stirred for 20 minutes, it was left over for 15 hours in a refrigerator. The reac- A mixture of 3 ml of methanol, 0.36 ml of 95% sulfuric acid and 1.2 mmol of the compound (Compound No. V-4) synthesized in the above procedure (1) was cooled with ice water and then stirred, to which a solution of 1.2 mmol of acetylacetone in 0.36 ml of acetic acid was added over 2 minutes. The resulting mixture was stirred for 20 minutes, and then at 80° C. for 8 hours. Then, the reaction mixture was cooled to room temperature, added with 2.5 g of sodium bicarbonate powder and 5 ml of water, and then stirred. After the pH of the resultant mixture was adjusted to pH 6 with acetic acid, 15 ml of water were added. The precipitate thus formed was collected by filtration and then dried in air. Yield: 71%. Its physicochemical properties are shown in Table 9. In addition, physicochemical properties of the compound (Compound No. II-C-1) synthesized in a similar manner are also shown in Table 9.

Further, physicochemical properties of other preparation intermediates synthesized in a similar manner to the above procedure (1) are also shown in Table 10.

TABLE 9

| Compound No. | MS (m/e) M+ | Melting Point or Decomposition point (°C.) | IR (KBr, cm$^{-1}$) |
| --- | --- | --- | --- |
| II-C-1 | 285 | 212–215 | 3280, 3160, 2960, 1590, 1550, 1470, 1390, 1370, 1330, 1170, 1050, 820, 800, 590 |
| II-C-2 | 309 | 172–175 | 3400–2800, 3350, 3070, 2950, 1725, 1600, 1550, 1440, 1350, 1310, 1290, 1170, 1130, 1060, 900, 780, 750, 710, 590, 530 |

TABLE 10

| Compound No. | MS (m/e) M+ | Melting Point or Decomposition point (°C.) | IR (KBr, cm$^{-1}$) | NMR (δ) |
|---|---|---|---|---|
| V-1 | 187 | 113-116 | 3360, 3350, 3300, 3220, 1600, 1470, 1340, 1330, 1290, 1140, 1090, 780, 680, 580, 510 | |
| V-2 | 221 | 155-158 Decomposition | 3370, 3330, 3130, 2970, 1590, 1560, 1460, 1330, 1270, 1160, 970, 830, 740, 690, 590, 550, 510 | |
| V-3 | 201 | 161-164 | 3300, 3250, 3010, 1610, 1490, 1300, 1160, 1140, 920, 820, 690, 600, 520. | d$_6$-DMSO:2.409(3H, s) 4.025br(2H, s) 6.840 (1H, dd, 8.5Hz, 1.8Hz) 6.901(1H, s) 7.048(1H d, 8.5Hz) 7.148(2H, s) 7.349(1H, d, 1.8Hz) |
| V-4 | 245 | 168-170 | 3350, 3310, 3250, 1680, 1630, 1590, 1440, 1350, 1330, 1300, 1270, 1170, 1160, 780, 700, 600 | |
| V-5 | 259 | 122-124 Decomposition | 3320, 3270, 2980, 1700, 1590, 1370, 1320, 1300, 1270, 1250, 1150, 1120, 770, 740, 700 | |

Compounds obtained in a similar manner to Synthesis Example 2 are shown in Table 11.

TABLE 11

| Compound No. | ⟨N-⟩ | R$^1$ | X$^1$ | X$^2$ | Z |
|---|---|---|---|---|---|
| I-21 | 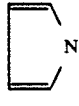 | H | OCH$_3$ | OCH$_3$ | N |
| I-22 | 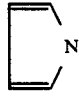 | CH$_3$ | OCH$_3$ | CH$_3$ | N |
| I-23 |  | CH$_3$ | OCH$_3$ | OCH$_3$ | N |
| I-24 |  | Cl | OCH$_3$ | OCH$_3$ | N |
| I-25 |  | COOCH$_3$ | OCH$_3$ | OCH$_3$ | N |
| I-26 |  | COOC$_2$H$_5$ | OCH$_3$ | CH$_3$ | N |
| I-27 |  | COOC$_2$H$_5$ | OCH$_3$ | OCH$_3$ | N |
| I-28 |  | CH$_3$ | CH$_3$ | OCH$_3$ | OCH$_3$ | N |
| I-29 |  | CH$_3$ | COOCH$_3$ | OCH$_3$ | CH$_3$ | N |
| I-30 |  | CH$_3$ | COOCH$_3$ | OCH$_3$ | OCH$_3$ | N |

Formulation examples and test will hereinafter be described. It should be borne in mind that the vehicles (diluents) and acids, their mixing ratios and effective components can vary in wide ranges respectively.

| Formulation Example 1: Wettable Powder | |
|---|---|
| Compound (Compound No. I-7) | 50 parts |
| A salt of ligninsulfonic acid | 5 parts |
| A salt of alkylsulfonic acid | 3 parts |
| Diatomaceous earth | 42 parts |

The above ingredients are mixed and ground into a wettable powder. For application, it is diluted with water.

| Formulation Example 2: Emulsion | |
|---|---|
| Compound (Compound No. I-9) | 25 parts |
| Xylene | 65 parts |
| Polyoxyethylene alkylaryl ether | 10 parts |

The above ingredients are mixed intimately into an emulsion. For application, it is diluted with water.

| Formulation Example 3: Granule | |
|---|---|
| Compound (Compound No. I-14) | 8 parts |
| Bentonite | 40 parts |
| Clay | 45 parts |
| A salt of ligninsulfonic acid | 7 parts |

The above ingredients are mixed intimately and after the addition of water, were kneaded and then formed into granules by an extruding granulator. They were then dried to provide a granular formulation, namely, a granule.

Test 1: Test on Herbicidal Activity by Foliar Application

Herbicidal solutions of each test compound, which had been prepared by dissolving at predetermined concentrations such a wettable powder of the test compound as that described in the above formulation example, and sprayed at dosages of 10 g/ha and 100 g/ha over foliar parts of *Amaranthus retroflexus* (Redroot pigweed), *Bidens pilosa* (Common blackjack), *Sinapis arvensis* (Wild mustard), *Stellaria media* (Common chickweed), *Cassia obtusifolia* (Sicklepod), *Solanum nigrum* (Black nightshade), *Abutilon theophrasti* (Velvetleaf), *Convolvulus arvensis* (Field bindweed), *Matricaria chamomilla* (Wild chamomile), *Setaria viridis* (Green foxtail), *Echinochloa frumentaceum* (Parnyard grass), *Avena fatua* (Wild oat), and *Digitaria adscendens* (Henry crabgrass) which had been allowed to grow individually to 2–4 leaf stage in pots. Fourteen days later after spraying of the test compound, its herbicidal activity was evaluated in accordance with the below-described system. The results are summarized in Table 12.

Ranking system:

Herbicidal activity

0: No effects
1: less than 31% of total kill
2: 31–50% of total kill
3: 51–70% of total kill
4: 71–90% of total kill
5: 91–100% of total kill

TABLE 12

| Compound No. | application dosage (g/ha) | A.r. | B.p. | S.a. | S.m. | C.o. | S.n. | A.t | C.a. | M.c. | S.v. | E.f. | A.f. | D.a. |
|---|---|---|---|---|---|---|---|---|---|---|---|---|---|---|
| I-1 | 10 | 5 | 5 | 5 | 5 | 5 | 3 | 3 | 0 | 5 | 5 | 0 | 0 | 5 |
| | 100 | 5 | 5 | 5 | 5 | 5 | 3 | 5 | 5 | 5 | 5 | 0 | 5 | 5 |
| I-2 | 10 | 5 | 5 | 5 | 5 | 5 | 3 | 4 | 5 | 5 | 5 | 0 | 5 | 2 |
| | 100 | 5 | 5 | 5 | 5 | 5 | 5 | 5 | 5 | 5 | 5 | 5 | 5 | 4 |
| I-3 | 10 | 5 | 5 | 5 | 5 | 5 | 5 | 5 | 4 | 5 | 5 | 5 | 5 | 5 |
| | 100 | 5 | 5 | 5 | 5 | 5 | 5 | 5 | 5 | 5 | 5 | 5 | 5 | 5 |
| I-4 | 10 | 5 | 5 | 5 | 5 | 5 | 5 | 5 | 3 | 5 | 5 | 5 | 5 | 4 |
| | 100 | 5 | 5 | 5 | 5 | 5 | 5 | 5 | 5 | 5 | 5 | 5 | 5 | 5 |
| I-5 | 10 | 5 | 5 | 5 | 5 | 5 | 5 | 5 | 2 | 5 | 5 | 5 | 5 | 5 |
| | 100 | 5 | 5 | 5 | 5 | 5 | 5 | 5 | 5 | 5 | 5 | 5 | 5 | 5 |
| I-6 | 10 | 5 | 5 | 5 | 5 | 5 | 5 | 5 | 5 | 5 | 5 | 5 | 5 | 4 |
| | 100 | 5 | 5 | 5 | 5 | 5 | 5 | 5 | 5 | 5 | 5 | 5 | 5 | 5 |
| I-7 | 10 | 5 | 5 | 5 | 5 | 5 | 5 | 2 | 0 | 5 | 5 | 4 | 5 | 0 |
| | 100 | 5 | 5 | 5 | 5 | 5 | 5 | 5 | 5 | 5 | 5 | 5 | 5 | 0 |
| I-8 | 10 | 5 | 5 | 5 | 5 | 5 | 5 | 5 | 3 | 5 | 5 | 3 | 5 | 0 |
| | 100 | 5 | 5 | 5 | 5 | 5 | 5 | 5 | 5 | 5 | 5 | 5 | 5 | 0 |
| I-9 | 10 | 5 | 5 | 5 | 5 | 5 | 5 | 5 | 5 | 5 | 5 | 5 | 5 | 0 |
| | 100 | 5 | 5 | 5 | 5 | 5 | 5 | 5 | 5 | 5 | 5 | 5 | 5 | 5 |
| I-10 | 10 | 1 | 5 | 5 | 5 | 0 | 4 | 5 | 3 | 4 | 0 | 0 | 4 | 0 |
| | 100 | 5 | 5 | 5 | 5 | 5 | 5 | 5 | 5 | 5 | 5 | 4 | 5 | 0 |
| I-11 | 10 | 5 | 5 | 5 | 5 | 5 | 5 | 5 | 5 | 5 | 5 | 5 | 5 | 0 |
| | 100 | 5 | 5 | 5 | 5 | 5 | 5 | 5 | 5 | 5 | 5 | 5 | 5 | 0 |
| I-12 | 10 | 5 | 5 | 5 | 5 | 4 | 5 | 5 | 5 | 5 | 5 | 4 | 5 | 4 |
| | 100 | 5 | 5 | 5 | 5 | 5 | 5 | 5 | 5 | 5 | 5 | 5 | 5 | 5 |
| I-13 | 10 | 5 | 5 | 5 | 4 | 2 | 2 | 3 | 3 | 0 | 5 | 5 | 3 | 0 |
| | 100 | 5 | 5 | 5 | 5 | 5 | 5 | 5 | 5 | 5 | 5 | 5 | 5 | 0 |
| I-14 | 10 | 5 | 5 | 5 | 5 | 3 | 5 | 3 | 5 | 5 | 5 | 5 | 5 | 0 |
| | 100 | 5 | 5 | 5 | 5 | 5 | 5 | 5 | 5 | 5 | 5 | 5 | 5 | 3 |
| I-15 | 10 | 4 | 0 | 5 | 3 | 0 | 0 | 0 | 0 | 0 | 0 | 0 | 0 | 0 |
| | 100 | 5 | 3 | 5 | 3 | 0 | 3 | 5 | 0 | 4 | 0 | 0 | 5 | 0 |
| I-16 | 10 | 5 | 5 | 5 | 4 | 0 | 0 | 4 | 4 | 0 | 0 | 0 | 0 | 0 |
| | 100 | 5 | 5 | 5 | 5 | 0 | 4 | 5 | 4 | 0 | 4 | 4 | 3 | 0 |
| I-17 | 10 | 5 | 2 | 5 | 2 | 0 | 3 | 3 | 0 | 0 | 0 | 0 | 0 | 0 |
| | 100 | 5 | 4 | 5 | 4 | 0 | 3 | 4 | 0 | 0 | 0 | 2 | 0 | 0 |
| I-18 | 10 | 5 | 2 | 5 | 5 | 0 | 5 | 2 | 4 | 0 | 3 | 3 | 5 | 0 |
| | 100 | 5 | 5 | 5 | 5 | 2 | 5 | 5 | 5 | 5 | 4 | 5 | 5 | 3 |
| I-19 | 10 | 0 | 0 | 4 | 2 | 0 | 0 | 0 | 0 | 0 | 0 | 0 | 0 | 0 |
| | 100 | 4 | 2 | 5 | 4 | 0 | 0 | 2 | 2 | 3 | 0 | 0 | 0 | 0 |
| I-20 | 10 | 5 | 5 | 5 | 5 | 3 | 3 | 5 | 5 | 5 | 2 | 0 | 0 | 0 |

TABLE 12-continued

| Compound No. | application dosage (g/ha) | A.r. | B.p. | S.a. | S.m. | C.o. | S.n. | A.t | C.a. | M.c. | S.v. | E.f. | A.f. | D.a. |
|---|---|---|---|---|---|---|---|---|---|---|---|---|---|---|
| | 100 | 5 | 5 | 5 | 5 | 5 | 5 | 5 | 5 | 5 | 4 | 4 | 4 | 0 |

Note)
A.r.: *Amaranthus retroflexus*
B.p.: *Bidens pilosa*
S.a.: *Sinapis arvensis*
S.m.: *Stellaria media*
C.o.: *Cassia obtusifolia*
S.n.: *Solanum nigrum*
A.t.: *Abutilon theophrasti*
C.a.: *Convolvulus arvensis*
M.c.: *Matricaria chamomilla*
S.v.: *Setaria viridis*
E.f.: *Echinochloa frumentaceum*
A.f.: *Avena fatua*
D.a.: *Digitaria adscendens*

Test 2: Germination Test of Seeds

Two sheets of filter paper were placed in a superposed relation in each of Petri dishes having a diameter of 9 cm. Water suspensions of each test compound (concentrations of the active ingredient: 1 ppm and 50 ppm) were separately poured in an amount of 5 ml per dish into the Petri dishes. Seeds of *Amaranthus retroflexus* (Redroot pigweed), *bidens pilosa* (Common blackjack), *Matricaria chamomilla* (Wild chamomile). *Solanum nigrum* (Black nightshade), *Echinochloa oryzicola* (Barnyard grass), *Cyperus iria* (Rice flatsedge) and *Setaria viridis* (Green foxtail) were placed at a rate of 10 seeds per dish in the Petri dishes. They were thereafter allowed to germinate in a constant-temperature chamber at 28° C. Fourteen days later after placement in the Petri dishes, the degrees of germination and growth inhibition were observed visually. The observation results were ranked in accordance with the below-described 6-stage system. The results are summarized in Table 13.

Growth inhibition rate

0: No inhibition
1: less than 31%
2: 2: 31–50%
3: 51–70%
4: 71–90%
5: 91–100%

TABLE 13

| Compound No. | Concentration (ppm) | A.r. | B.p. | M.c. | S.n. | E.o | C.i. | S.v. |
|---|---|---|---|---|---|---|---|---|
| I-1 | 1 | 0 | 0 | 0 | 0 | 0 | 0 | 0 |
| | 50 | 4 | 3 | 5 | 4 | 4 | 4 | 5 |
| I-2 | 1 | 0 | 0 | 0 | 0 | 0 | 0 | 0 |
| | 50 | 4 | 4 | 5 | 4 | 5 | 5 | 5 |
| I-3 | 1 | 0 | 0 | 0 | 0 | 0 | 0 | 0 |
| | 50 | 4 | 4 | 5 | 3 | 4 | 5 | 5 |
| I-4 | 1 | 0 | 0 | 0 | 0 | 0 | 0 | 0 |
| | 50 | 4 | 4 | 5 | 4 | 5 | 5 | 5 |
| I-5 | 1 | 4 | 3 | 4 | 3 | 4 | 4 | 4 |
| | 50 | 5 | 4 | 4 | 4 | 5 | 4 | 5 |
| I-6 | 1 | 1 | 3 | 0 | 0 | 3 | 3 | 3 |
| | 50 | 5 | 4 | 5 | 4 | 5 | 4 | 5 |
| I-7 | 1 | 4 | 4 | 5 | 4 | 5 | 5 | 5 |
| | 50 | 4 | 4 | 5 | 5 | 5 | 5 | 5 |
| I-8 | 1 | 5 | 4 | 5 | 4 | 5 | 5 | 5 |
| | 50 | 5 | 5 | 5 | 4 | 5 | 5 | 5 |
| I-9 | 1 | 5 | 4 | 5 | 5 | 4 | 4 | 5 |
| | 50 | 5 | 5 | 5 | 5 | 5 | 5 | 5 |
| I-10 | 1 | 5 | 2 | 5 | 5 | 3 | 0 | 2 |
| | 50 | 5 | 5 | 5 | 5 | 4 | 5 | 5 |
| I-11 | 1 | 2 | 2 | 2 | 2 | 0 | 2 | 3 |
| | 50 | 4 | 3 | 5 | 5 | 5 | 4 | 5 |
| I-12 | 1 | 0 | 0 | 0 | 0 | 0 | 0 | 0 |
| | 50 | 4 | 2 | 5 | 5 | 5 | 4 | 5 |
| I-13 | 1 | 0 | 0 | 4 | 0 | 0 | 0 | 0 |
| | 50 | 2 | 2 | 4 | 3 | 3 | 4 | 4 |
| I-14 | 1 | 0 | 0 | 4 | 2 | 0 | 2 | 0 |
| | 50 | 4 | 3 | 4 | 4 | 4 | 5 | 5 |
| I-15 | 1 | 4 | 0 | 0 | 4 | 0 | 4 | 0 |
| | 50 | 5 | 5 | 5 | 5 | 4 | 5 | 5 |
| I-16 | 1 | 4 | 4 | 0 | 4 | 5 | 4 | 4 |
| | 50 | 5 | 5 | 5 | 5 | 5 | 5 | 5 |
| I-17 | 1 | 4 | 0 | 0 | 3 | 3 | 3 | 3 |
| | 50 | 4 | 4 | 4 | 5 | 4 | 5 | 5 |
| I-18 | 1 | 4 | 4 | 4 | 4 | 5 | 4 | 5 |
| | 50 | 4 | 4 | 5 | 5 | 5 | 5 | 5 |
| I-19 | 1 | 3 | 0 | 0 | 0 | 0 | 0 | 0 |
| | 50 | 5 | 5 | 4 | 5 | 4 | 5 | 5 |
| I-20 | 1 | 4 | 4 | 4 | 4 | 5 | 5 | 5 |
| | 50 | 5 | 4 | 5 | 4 | 5 | 5 | 5 |

Note)
A.r.: *Amaranthus retroflexus*
B.p.: *Bidens pilosa*
M.c.: *Matricaria chamomilla*
S.n.: *Solanum nigrum*
E.o.: *Echinochloa oryzicola*
C.i.: *Cyperus iria*
S.v.: *Setaria viridis*

We claim:

1. An N-substituted-3-(nitrogen-containing 5-membered ring)benzenesulfonamide derivative of the formula (I):

$$\text{(I)}$$

wherein ⟨N-⟩ is pyrrolidinyl, 2,5-dimethylpyrrolyl,

-continued

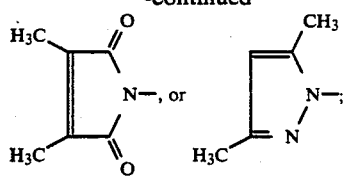

$R^1$ is H, Cl, $C_1$–$C_3$ alkyl or $C_1$–$C_4$ alkoxycarbonyl; Z is CH $X^1$ is $C_1$–$C_3$ alkyl, $C_1$–$C_3$ alkoxyl or Cl; and $X^2$ is $C_1$–$C_3$ alkyl or $C_1$–$C_3$ alkoxyl.

2. A derivative of claim 1, wherein 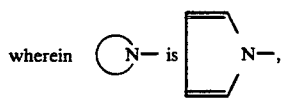

$R^1$ is H, Cl, $CH_3$, $COOCH_3$ or $COOC_2H_5$, $X^1$ is $OCH_3$, and $X^2$ is $OCH_3$.

3. A derivative of claim 1, wherein

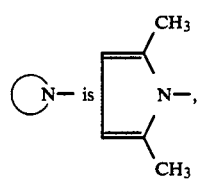

$R^1$ is H, Cl, $CH_3$, $COOCH_3$ or $COOC_2H_5$, $X^1$ is $OCH_3$, and $X^2$ is $OCH_3$.

4. A derivative of claim 1, wherein

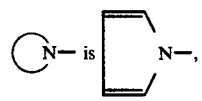

$R^1$ is $COOCH_3$, $X^1$ is Cl, and $X^2$ is $OCH_3$.

5. A derivative of claim 1, wherein

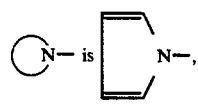

$R^1$ is $COOCH_3$, $X^1$ is $CH_3$, and $X^2$ is $CH_3$.

6. A derivative of claim 1, wherein

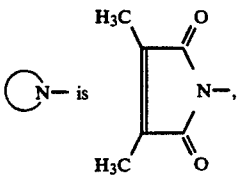

$R^1$ is H, Cl, $CH_3$ or $COOCH_3$, $X^1$ is $OCH_3$, and $X^2$ is $OCH_3$.

7. A derivative of claim 1, wherein

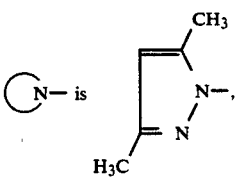

$R^1$ is Cl or $COOCH_3$, $X^1$ is $OCH_3$, and $X^2$ is $OCH_3$.

8. A herbicidal composition comprising a herbicidally effective amount of an N-substituted-3-(nitrogen-containing 5-membered ring)benzenesulfonamide derivative of claim 1 and an agronomically-acceptable vehicle or diluent.

9. A method for the control of monocotyledonous or dicotyledonous weeds on an agricultural or non-agricultural land, which comprises applying to the agricultural or non-agricultural land an effective amount of a composition according to claim 15.

* * * * *

UNITED STATES PATENT AND TRADEMARK OFFICE
CERTIFICATE OF CORRECTION

PATENT NO. : 5,242,894
DATED : April 21, 1992
INVENTOR(S) : Hideo Arabori, et. al.

It is certified that error appears in the above-indentified patent and that said Letters Patent is hereby corrected as shown below:

Column 26, line 42, change "according to claim 15" to --according to claim 8--.
Column 15, line 26, change "2-(aminosulfonyll)" to --2-(aminosulfonyl --.
Column 23, line 25, change "bidens pilosa" to Bidens pilosa--.

Signed and Sealed this

Twenty-second Day of November, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,242,894
DATED : September 7, 1993
INVENTOR(S) : Hideo ARABORI et al It is certified that error appears in the above-indentified patent and that said Letters Patent is hereby corrected as shown below:

Column 15, line 26, change "2-(aminosulfonyl1)" to --2-(aminosulfonyl)--.

Column 23, line 25, change "*bidens pilosa*" to --*Bidens pilosa*--.

Column 26, line 42 change "according to claim 15" to --according to claim 8--.

This certificate supersedes Certificate of Correction issued November 22, 1994.

Signed and Sealed this

Fourteenth Day of March, 1995

Attest:

BRUCE LEHMAN

Attesting Officer    Commissioner of Patents and Trademarks